United States Patent [19]
Rattner

[11] Patent Number: 5,284,143
[45] Date of Patent: Feb. 8, 1994

[54] APPARATUS FOR TREATING BONE PATHOLOGIES WITH ACOUSTIC ENERGY

[75] Inventor: Manfred Rattner, Grossenseebach, Fed. Rep. of Germany

[73] Assignee: Siemens Aktiengesellschaft, Munich, Fed. Rep. of Germany

[21] Appl. No.: 885,749

[22] Filed: May 19, 1992

[30] Foreign Application Priority Data

Jun. 13, 1991 [DE] Fed. Rep. of Germany ....... 4119524

[51] Int. Cl.$^5$ .............................. A61B 6/00; A61B 8/00; A61N 1/00
[52] U.S. Cl. .................................................. 128/653.1
[58] Field of Search ................... 606/128; 128/24 EL, 128/653.1, 660.03

[56] References Cited

U.S. PATENT DOCUMENTS

| | | | |
|---|---|---|---|
| 4,697,588 | 10/1987 | Reichenberger | 128/328 |
| 4,928,672 | 5/1990 | Grasser et al. | 606/128 |
| 4,947,830 | 8/1990 | Rattner et al. | 128/660.03 X |
| 4,979,501 | 12/1990 | Valchanov et al. | 128/419 F X |
| 5,076,277 | 12/1991 | Iwama et al. | 128/660.03 |
| 5,081,984 | 1/1992 | Wess et al. | 128/24 EL |
| 5,178,135 | 1/1993 | Uchiyama et al. | 128/660.03 X |

FOREIGN PATENT DOCUMENTS

| | | |
|---|---|---|
| 0373967 | 6/1990 | European Pat. Off. |
| 0391378 | 10/1990 | European Pat. Off. |
| 0397056 | 11/1990 | European Pat. Off. |
| WO90/05492 | 5/1990 | PCT Int'l Appl. |

OTHER PUBLICATIONS

"Stosswellen in der Medizin," Forssmann et al., Medizin in unserer Zeit, vol. 4, No. 1 (1980), pp. 10–14.

Primary Examiner—Francis Jaworski
Attorney, Agent, or Firm—Hill, Steadman & Simpson

[57] ABSTRACT

An apparatus for treating bone pathologies with acoustic waves includes a source of focused acoustic waves, a system for displacing the focus of the acoustic waves, and a system for locating the boundary surface between the bone to be treated and surrounding tissue. The locating system generates signals corresponding to the position of the boundary surface. A control unit, which operates the focused displacing system, is supplied with the signals identifying the position of the boundary surface, so that the focused displacing system is controlled to maintain the focus substantially at the boundary surface, independently of the position of the acoustic wave source.

44 Claims, 4 Drawing Sheets

APPARATUS FOR TREATING BONE PATHOLOGIES WITH ACOUSTIC ENERGY

BACKGROUND OF THE INVENTION

1. Field of the Invention

The present invention is directed to an apparatus for treating bone pathologies with acoustic energy, administered by acoustic waves.

2. Description of the Prior Art

Recent experiments have shown that the healing process for certain bone pathologies can be accelerated, beneficially influenced, or initiated by applying acoustic energy, particularly focused shockwaves, to a bone region. Such treatment is described in PCT Application WO88/09190, corresponding to U.S. Pat. No. 4,979,501. As described therein, such treatment has heretofore been implemented using lithotriptors, also known as extracorporeal shockwave devices (ESWD). These are shockwave therapy devices which are normally used for the purpose of treating stone pathologies, for example, nephrolithiasis, with focused shockwaves.

In treating bone pathologies, particularly pathologies in a region of the long bones of the extremities, with focused shockwaves, it is necessary, while retaining the acoustic coupling of the therapy apparatus with the body part to be treated, to execute a relative motion between the focus of the acoustic waves and the body part to be treated, such that the focus of the acoustic waves is moved along the zone requiring treatment. When treating the fracture of a long bone, for example, this means that the focus of the acoustic waves must be moved along the fracture break. In order to maintain the stress to the patient, resulting from the application of acoustic energy, at as low a level as possible, it is preferable to irradiate the bone with acoustic shockwaves which proceed to the treatment location along a direct path. This means that the acoustic waves, for example, should not be required to initially propagate through a bone wall disposed diametrically opposite the location to be treated, because this would result in excessively high acoustic losses. It is thus necessary to move the therapy apparatus around the body part to be treated, for example, in an approximately circular motion. A further problem is that the distance of the bone from the surface of the body part to be treated is not constant, so that the spacing of the focus from the surface of the body part must be constantly adjusted, by setting different spacings, during the displacement of the focus and the body part containing the bone requiring treatment relative to each other.

These requirement are extremely difficult to satisfy with a lithotriptor, because the patient support as well as its adjustment possibilities are adapted for a different type of treatment. Moreover, the adjustment possibilities of the shockwave generator and of the locating system are designed for charging the patient with shockwaves in the trunk region, and once alignment of the patient and the shockwave generator relative to each other has been achieved, the located position is essentially retained, and is varied only for the purpose of making corrections and small adjustments as may become necessary because of changes in the position of the calculus occurring during the treatment. Therefore, treatment of bone pathologies can only be implemented in a complicated fashion using conventional lithotriptors, and thus involves risks for the patient due to the danger of incorrect operation of the treatment apparatus as well as due to locating errors.

SUMMARY OF THE INVENTION

It is an object of the present invention to provide an apparatus for treating bone pathologies with acoustic energy in the form of focused acoustic waves in a simple and reliable manner.

The above object is achieved in accordance with the principles of the present invention in an apparatus for treating bone pathologies with acoustic energy which includes a source of focused acoustic waves (such as focused shockwaves), means for displacing the focus of the acoustic waves, means for locating the boundary surface between the bone to be treated and surrounding tissue which generates signals corresponding to the position of the boundary surface, and control means to which these signals are supplied which actuates the focus displacing means so that the focus lies substantially at the boundary surface, independently of the position of the acoustic wave source. The apparatus of the invention thus significantly simplifies the treatment of bone pathologies, because it ensured that the focus will be automatically displaced during the relative adjustment of the source and the body part to be treated which takes place during the treatment, so that the focus will always be maintained substantially at the boundary surface between the bone and surrounding tissue. It has been shown that the treatment is particularly effective when the focus, i.e., the center of the focal zone, lies in the boundary surface between the bone to be treated and the tissue surrounding this bone, i.e., in the region of the periosteum. At the same time, an improved degree of patient safety is achieved, because operating errors are not possible due to the automatic focus displacement.

In an embodiment of the invention, the focus lies on the acoustic axis of the acoustic wave source, and the locating means identifies the intersection of the acoustic axis with the boundary surface, and the displacing means displaces the focus in the direction of the acoustic axis. The automatic displacement of the focus in this embodiment involves particularly little outlay, because the direction of locating and the direction of displacement are identical.

In a preferred embodiment of the invention, means for identifying the course of a zone to be treated generates signals corresponding to this course, and the signals are used to adjust the position of the acoustic wave source, and thus the position of the focus. The control means, to which the signals from the identification means are supplied, actuates the adjustment means with at least one degree of freedom, so that the focus is always located in the zone to be treated independently of the position of the source with respect to the other degrees of freedom. This assures not only that the focus will lie in the boundary surface between the bone and tissue, but will also lie in the zone to be treated. It is preferable for the control means to actuate the adjustment means so that the focus is located in that region of the zone to be treated which is directly adjacent to the source, because it is then assured that the acoustic energy proceeds along a direct path to the zone to be treated. In a further embodiment of the invention, the control means actuates the adjustment means so that the focus zone automatically moves along the course of the zone to be treated, thereby further simplifying the treatment and providing a further increase in patient safety.

Preferably the locating means includes a pressure sensor disposed in the propagation path of the acoustic waves, means for pulse-like actuation of the acoustic wave source, and means for measuring the time between two pulse-like output signals of the pressure sensor, which occur in sequence following the pulse-like actuation of the source. A signal corresponding to this time is supplied to the control means. The two pulse-like output signals of the pressure sensor are respectively formed by the signal which first arises upon passage of the generated acoustic wave through the pressure sensor, the signal which subsequently arises when the portions of the generated acoustic wave which are reflected at the bone to be treated pass through the pressure sensor. The time which has elapsed between these pulse-like output signals of the pressure sensor is thus a measure of the spacing of the boundary surface from the pressure sensor. Because the spacing of the pressure sensor from the focus of the acoustic waves is known, the control unit actuates the means for displacing the focal zone so that the time between the two pulse-like output signals corresponds to the distance (or more precisely, to twice the distance) between the pressure sensor and the focus. This means that the focus lies in the boundary surface between the bone and tissue, as desired. Because this control event may make it necessary to multiply actuate the source, the means for pulse-like actuation of the source can actuate the source to generate acoustic waves of diminished intensity, to protect the patient and minimize patient discomfort.

In a further embodiment of the invention, the locating means is an ultrasound system by which an ultrasound image of a slice of the patient containing the focus can be produced, for example a sector scanner. The locating means in this embodiment also includes means for identifying an intensity discontinuity in the generated ultrasound image which corresponds to the boundary layer, and means for comparing the location of the intensity discontinuity with the location of the focus in the ultrasound image. An output signal is supplied to the control means given coincidence of the location of the intensity discontinuity and the location of the focus. This output signal causes actuation of the means for displacing the focus in a manner so that such coincidence in the generated ultrasound image is maintained.

The means for comparing may also include means for generating a trend signal, which indicates whether the focus must be moved closer to the body part to be treated, or must be moved away from it. In a further modification of this embodiment, the means for identification and/or the means for locating may be an ultrasound tomography system which generates slices having a defined position relative to the acoustic wave source, which can be displayed in ultrasound images, and means for marking can be provided which marks, within the ultrasound images, the regions of the zone to be treated. Calculating means can be provided which, with respect to a marked region, supplies the control means with signals causing the control means to actuate the adjustment means so that the focus lies in the marked region. A plurality of image memories may be provided, in which ultrasound images registered for different positions of the ultrasound applicator relative to the body part to be treated can be stored. The calculating means can then calculate the spatial path of the zone to be treated and/or the spatial path of the boundary surface with respect to the regions of the zone to be treated which are marked in the individual ultrasound images. Corresponding signals are then supplied to the control unit which actuates the adjustment means and/or the means for displacement in a corresponding manner. It is thus possible automatically to adjust the source on the basis of the information acquired with the ultrasound images with a corresponding automatic displacement of the focus, so that the focus is moved along the region to be treated and always lies in the boundary surface between the bone and surrounding tissue. The ultrasound applicator of the ultrasound tomography system can be received in a central bore of the acoustic wave source.

In a further embodiment of the invention, the means for locating and/or the means for identification may be an x-ray (radiological) diagnostics system having an x-ray source and a radiation receiver disposed opposite the x-ray source, with which x-ray images of the body part to be treated can be produced from different angles. In a preferred version of this embodiment, the beam path of the x-ray system proceeds through a central region of the acoustic wave source which is transparent for x-rays.

In a further version of the embodiment using an x-ray locating system, at least two image stores are provided for respectively storing two x-ray images obtained from defined, different angles, and means for marking the path of a zone to be treated in the x-ray images is provided. An electronic calculating unit is also provided which, with reference to the paths marked in the x-ray images, calculates the actual spatial path of the zone to be treated and/or the spatial path of the boundary surface between the bone and surrounding tissue along the zone to be treated. The calculating unit supplies corresponding signals to the control unit, which actuates the adjustment means and/or the means for displacement based on these signals. The source can thereby be automatically adjusted, with automatic displacement of the focus, solely on the basis of the information acquired by two x-ray images, so that the focus is moved along the region to be treated and always lies in the boundary surface between the bone and surrounding tissue.

The adjustment means can adjust the acoustic wave source along a circular path, as well as along an axis which intersects the plane of the circular path at a right angle.

The means for displacing the focus may be a means for displacing the acoustic wave source along its acoustic axis, or the source may contain focusing means for the acoustic waves, such as in the form of an acoustic lens having a variable focal length.

A method for treating bone pathologies corresponding to the above apparatus is also disclosed, the method including the basic steps of charging a pathological region of a bone with focused acoustic shockwaves, particularly shockwaves, with the boundary surface between the periosteum and surrounding tissue proceeding substantially through the focus of the acoustic waves.

DESCRIPTION OF THE PREFERRED EMBODIMENTS

Figure 1:
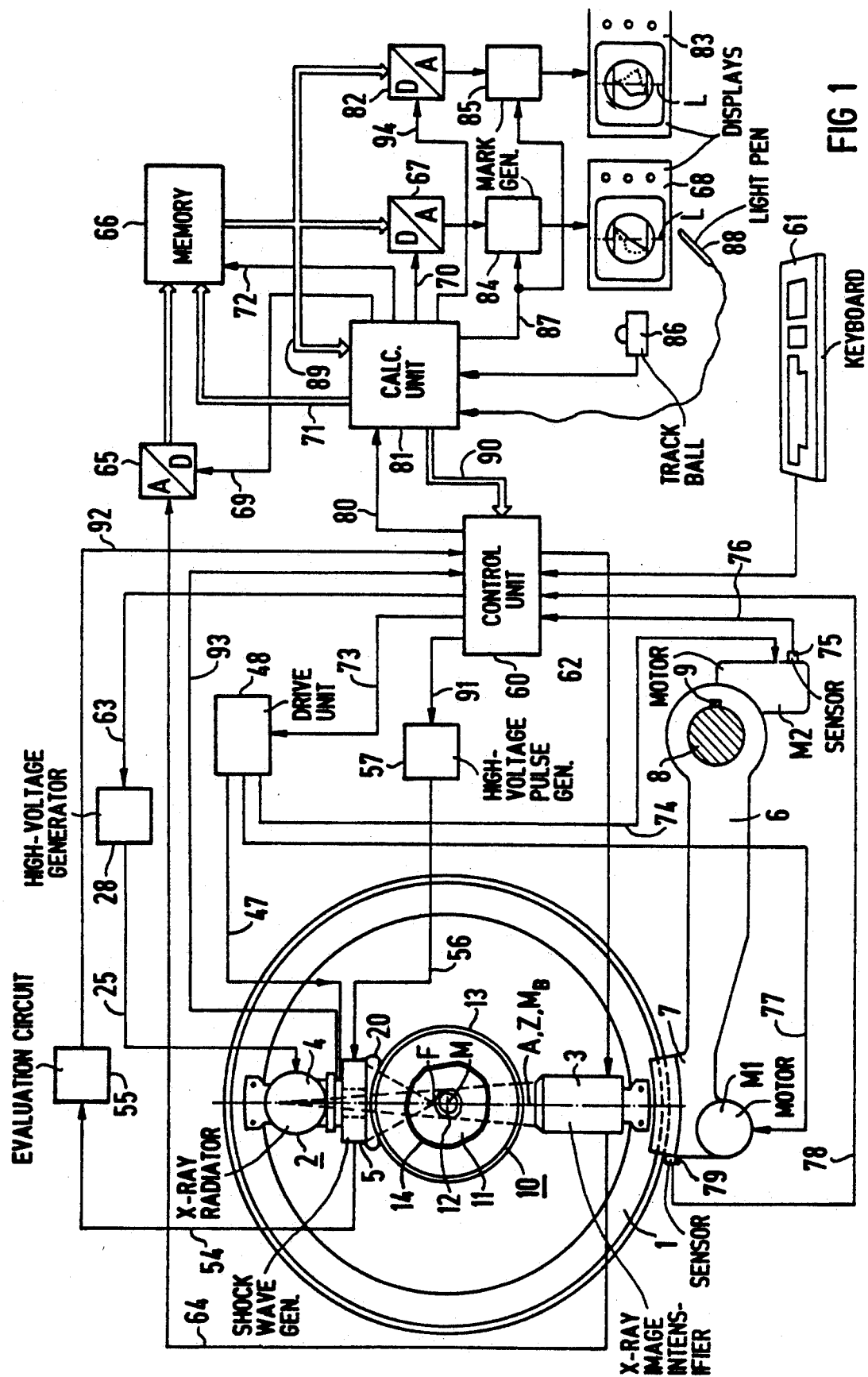
FIG. 1 is an end elevational view of an apparatus for treating bone pathologies with acoustic waves constructed in accordance with the principles of the present invention, with associated electronic components being schematically indicated including a block circuit diagram.

The embodiment of the invention shown in FIG. 1 includes a circular carrier 1 having an approximately T-shaped cross section. A treatment head 2 and an x-ray image intensifier 3 disposed opposite the treatment head 2 are attached to the inner circumference of the carrier 1. The treatment head 2 is described in greater detail in connection with FIG. 2, and includes an x-ray radiator 4 and a shockwave generator 5. The shockwave generator 5 includes a shockwave source (not shown in FIG. 1) as the source of acoustic waves. The shockwave generator 5 generates an output in the form of focused shockwaves onto a focus F, and has a central region which is transmissive for x-rays. The x-ray radiator 4 and the shockwave generator 5 are connected to each other so that the x-ray beam, indicated with dashed lines in FIG. 1, passes through the region of the shockwave generator 5 which is transparent for x-rays. The x-ray beam is incident on the input luminescent screen of the x-ray image intensifier 3. The components are arranged so that a central ray Z of the x-ray beam, the acoustic axis A of the shockwave source of the shockwave generator 5, and the middle axis $M_B$ of the x-ray image intensifier 3 coincide.

The carrier 1 is connected to a bracket 6 so that the crossbar of its T-shaped cross section is received in sliding fashion in a guide 7 in the bracket 6. A motor M1 is attached to the bracket 6, which has a drive shaft engaging teeth (not specifically shown) at the circumference of the carrier 1 via suitable gearing (not shown) for the purpose of rotating the carrier 1 around its center axis M.

The bracket 6 is attached so as to be longitudinally displaceable, but non-rotatable, on a guide rod 8. A further motor M2, which interacts via a further gearing (not shown) with a toothed rack 9, connected to and extending along the guide rod 8, serves the purpose of adjusting the position of the bracket 6, together with the carrier 1, along the guide rod 8.

The guide rod 8 is mounted on a pedestal (not shown) so that the center axis M of the carrier 1, which proceeds parallel to the guide rod 8, is oriented at least approximately horizontally. A tubular coupling element 10 is also connected to the pedestal so that its center axis substantially coincides with the center axis M of the carrier 1.

Figure 3:
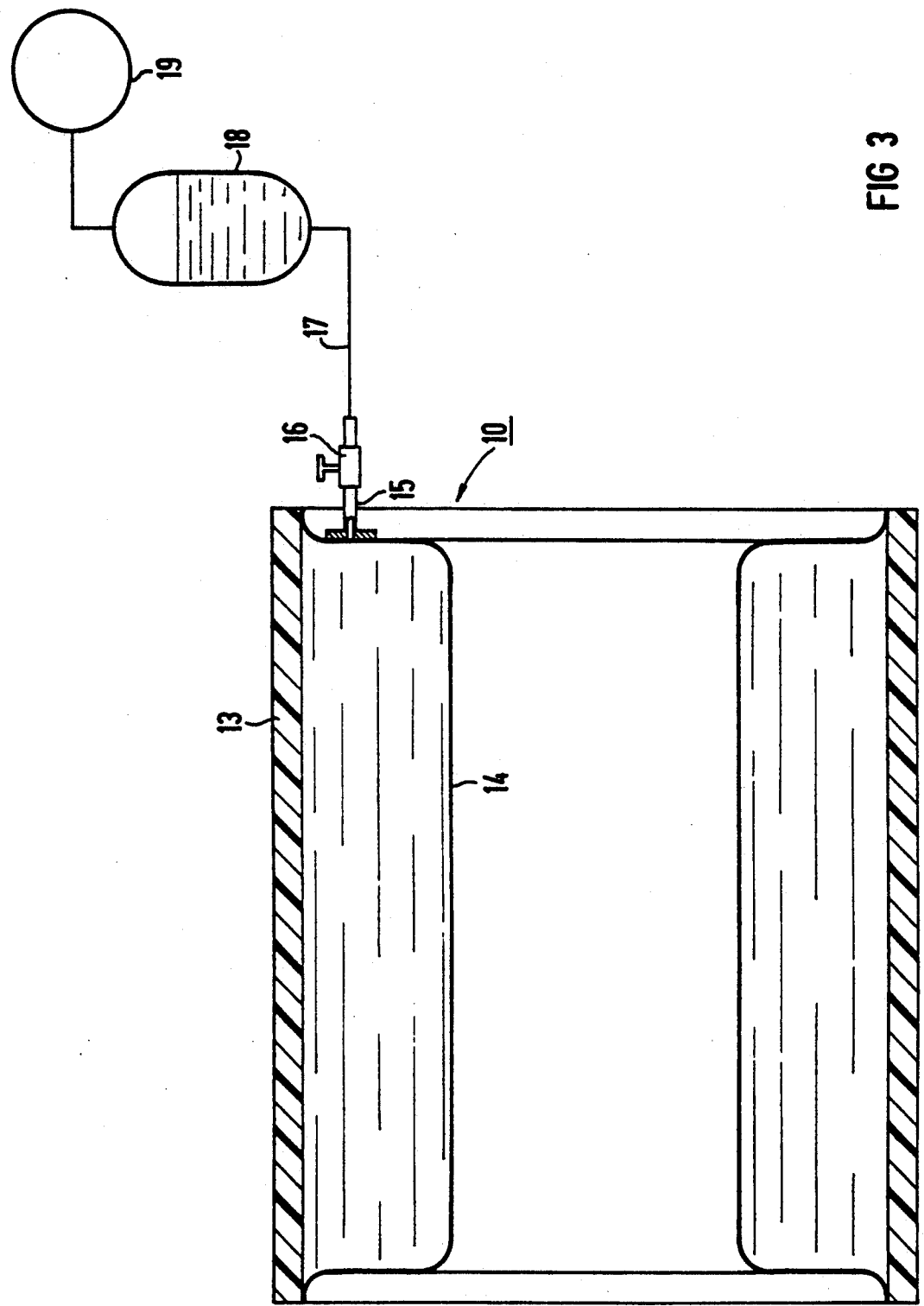
FIG. 3 is a longitudinal sectional view through an acoustic coupling element used in the apparatus of FIG. 1, constructed in accordance with the principles of the present invention.

The coupling element 10, shown in greater detail in FIG. 3, acoustically couples the shockwave generated by the shockwave generator 5 into an extremity to be treated, for example a thigh 11 containing a femur 12 to be treated. The coupling element 10 consists of a rigid, hollow-cylindrical outer part 13 and a hose-like, flexible inner part 14. The ends of the inner part 14 are provided with radially outwardly widened sections having circumferential edges joined to the outer part 13 in liquid-tight fashion, for example by gluing. The annular space limited by the outer part 13 and the inner part 14 is filled with an acoustic propagation medium for the shockwaves emanating from the shockwave generator 5. In order to couple these shockwaves into the body part to be treated with minimum loss, a liquid having an acoustic impedance substantially corresponding to that of the patient is provided as the acoustic propagation medium. Assuming the patient is a human, the acoustic propagation medium will thus have an acoustic impedance approximating the acoustic of human tissue, and may be, for example, water. The outer part 13 and the inner part 14 consist of materials having an acoustic impedance substantially corresponding to that of the propagation medium, and thus in the present example substantially corresponding to animal or human tissue. Polymethylpentene (TPX) is suitable as material for the outer part 13, and latex is suitable as the material for the inner part 14.

A connecting sleeve 15 with a shut-off valve 16 is provided in the region of the widened edge sections. The connecting sleeve 15 is connected to a valve 16 which is in turn connected to a line 17 leading to compensation vessel 18 containing the acoustic propagation medium, such as water. The compensation vessel 18 can be charged with a pressure greater than atmospheric pressure by a schematically indicated pressure source 19.

Prior to treatment, an extremity to be treated, which may be coated with a water-containing gel of the type employed in ultrasound examinations in order to improve the acoustic coupling, is introduced into the coupling element 10. Water situated in the annular space between the outer part 13 and the inner part 14 is thereby forced into the compensation vessel 18 under certain circumstances. When the extremity assumes the desired position within the coupling element 10, the compensation vessel 18 is charged with a pressure adapted to the particular treatment case. Water situated in the compensation vessel 18 is thereby forced into the annular space between the outer part 13 and the inner part 14. The shut-off valve 16 is closed as soon as the desired pressure is reached. The line 17 can then be separated from the connecting sleeve 15, after first venting any over-pressure which may be present within the compensation vessel 18.

Figure 2:
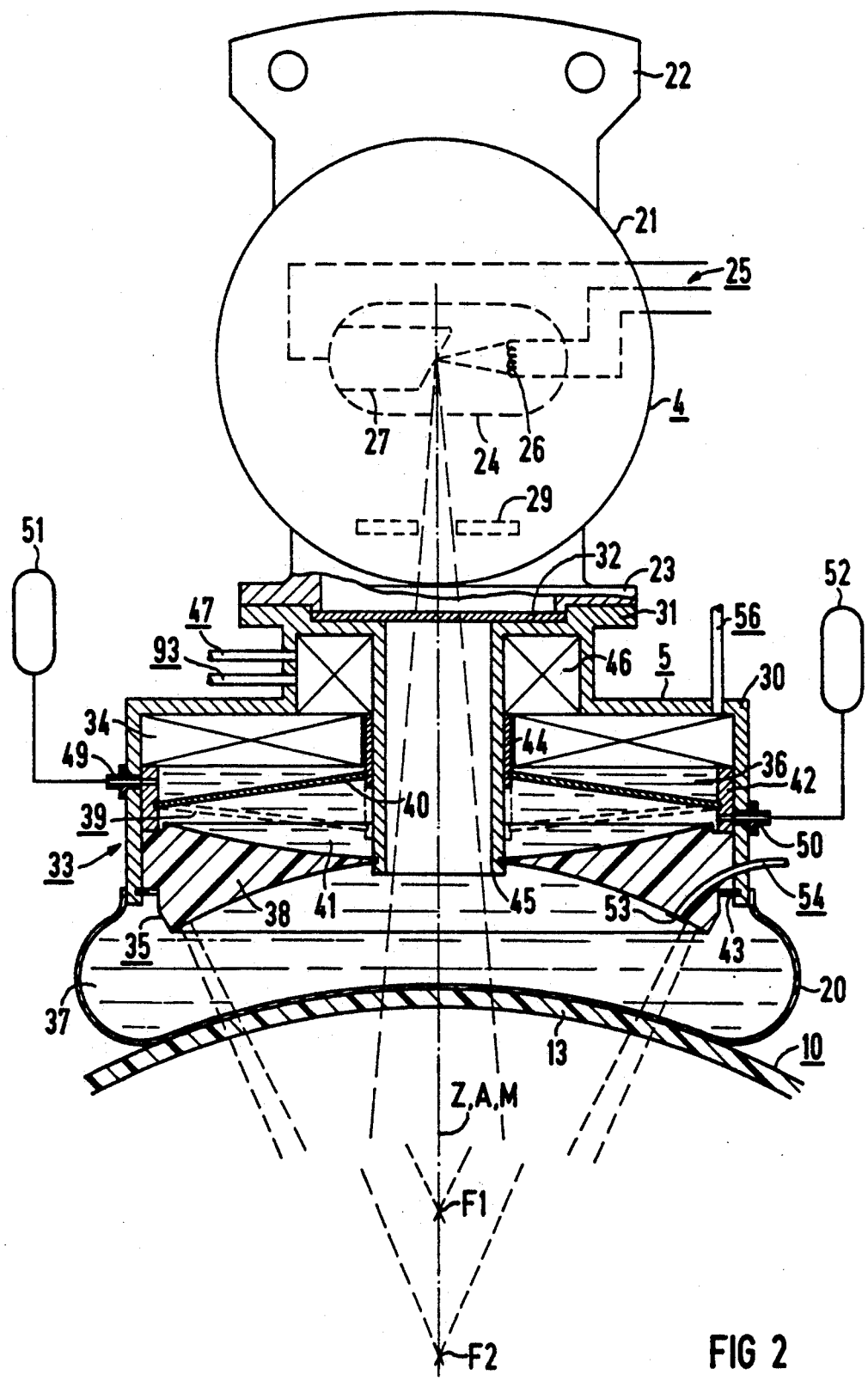
FIG. 2 is an enlarged longitudinal sectional view of the source for acoustic waves used in the apparatus of FIG. 1, constructed in accordance with the principles of the present invention.

As shown in FIGS. 1 and 2, the shockwave generator 5 presses against the outer surface of the outer part 13 of the coupling element 10 with a flexible coupling pillow 20. In order to facilitate the relative motion between the coupling pillow 20 and the outer part 13, which occur when the carrier 1 is rotated by the motor M1, or when the bracket 6 together with the carrier 1 are adjusted along the rod 8 with the motor M2, the outer surface of the outer part 13 can be coated with an anti-seizing agent, for example a water-containing gel.

A shown in FIG. 2, the treatment head 2 contains the aforementioned x-ray radiator, generally referenced 4, and contains the aforementioned shockwave generator, generally referenced 5.

The x-ray radiator 4 shown in FIG. 2 has a protective housing 21, provided with a fastening part 22 and with a fastening flange 23. The fastening part 22 is for fastening the treatment head 2 to the carrier 1 and the fastening flange 23 is for connecting the x-ray radiator 4 to the shockwave generator 5. An x-ray tube 24, shown with dashed lines in FIG. 2, is disposed in the interior of the protective housing 21. The x-ray tube 24 is connected to a power cable 25 (schematically indicated) which leads to a high-voltage generator 28 (shown in FIG. 1) which supplies the filament voltage for the cathode 26 and the tube voltage between the cathode 26 and the anode 27, which are required for operation of the x-ray tube 24. A primary radiation diaphragm 29 is also contained in the protective housing 21, which gates the x-ray beam with a circular cross section. The aperture angle of diaphragm 29 is selected so that the x-ray beam is of a size substantially coextensive with the input luminescent screen of the x-ray image intensifier 3, when the x-ray beam reaches the location of the input luminescent screen.

The shockwave generator 5 is connected to the x-ray radiator 4 so that the center axis of the shockwave generator 5 coincides with the central ray Z of the x-ray beam. The shockwave generator 5 has a housing 30 which is closed liquid-tight with the coupling pillow 20 at its distal end relative to the x-ray radiator 4. At its end proximate to the x-ray radiator 4, the housing 30 has a mounting flange 31 which presses against the fastening flange 23 of the protective housing 21. The two components are connected to each other by screws, with only the center lines of two screws being schematically indicated with dot-dash lines. A separating disc 32, which is transparent for x-rays and separates the shockwave generator 5 from the x-ray radiator 4 in liquid-tight fashion is disposed between the x-ray radiator 4 and the shockwave generator 5. A shockwave source, generally referenced 33, is disposed in the interior of the housing 30. The shockwave source 33 includes an electromagnetic pressure pulse source 34 (of the type known to those skilled in the art and, therefore, not shown in detail), and an acoustic positive lens generally referenced 35. Both have a central opening through which a tubular interior wall 45 of the housing 30 extends. The inside diameter of the interior wall 45 is dimensioned so that the x-ray beam can pass through the tubular interior wall 45 unimpeded. The pressure pulse 34, for example, may be an electromagnetic pressure pulse source of the type disclosed, for example, in European Application 0 188 750, corresponding to U.S. Pat. No. 4,697,588 and European Application 0 301 360, corresponding to U.S. Pat. No. 4,928,672. A positive lens 35 is disposed in the propagation path for the acoustic waves, and is a vario-lens having a variable focal length. The space situated between the pressure pulse source 34 and the positive lens 35 is filled with acoustic propagation medium 36 and the space between the positive lens 35 and the coupling pillow 20 is filled with acoustic propagation medium 37, both of which may be water.

The positive lens 35 is formed by a solid lens 38 and a liquid lens generally referenced 39. The solid lens is bi-concave, and consists of a material, for example polystyrol, in which the speed of sound is higher than the speed of sound in the water 37 provided as the acoustic propagation medium. The solid lens 38 consequently acts as positive lens. The liquid lens 39 is formed by a lens liquid 41 enclosed between an entry wall 40 and that side of the solid lens 38 facing toward the pressure pulse source 34. The outer edge of the entry wall 40 is received liquid-tight in a circumferential channel of a retainer ring 42. The retainer ring 42 is axially non-displaceably received between the pressure pulse source 34 and the solid lens 38. The solid lens 38 is held axially non-displaceable by a snap ring 43. The inner circumferential edge of the entry wall 40 is received in a circumferential channel of a sleeve 44, placed liquid-tight around the inner wall 45. The sleeve 44 is longitudinally displaceable along the inner wall 45 with an adjustment mechanism 46 (schematically shown), which may be an electric motor with suitable gearing. The adjustment mechanism 46 is electrically connected to a drive unit 48 (shown in FIG. 1) via a line 47. The focal length of the liquid lens 39, and thus the overall focal length of the positive lens 35, can be varied by displacing the sleeve 44 between one extreme position shown in solid lines in FIG. 2, and another extreme position indicated with dashed lines.

When, as in the case of the illustrated exemplary embodiment, the lens liquid 41 is a liquid in which the speed of sound is lower than in speed of sound in the water 36 provided as the acoustic propagation medium, the liquid lens 39 acts as a positive lens for when the sleeve 44 is in the extreme position shown with solid lens in FIG. 2. As the sleeve 44 is gradually adjusted in the direction toward its other extreme position, the focusing effect of the liquid lens 39 is reduced, and gradually changes into a slightly defocusing effect. In the extreme position indicated with dashed lines, the liquid lens 39 thus acts as a diverging lens. This means that the focus F1 for shockwaves generated by the pressure pulse source 34 and focused by the positive lens 35 will be situated closer to the shockwave generator 5 when the sleeve 44 is in the extreme position shown with solid lines in FIG. 2, and the focus F2 will be at a greater distance therefrom when the sleeve 44 is in the extreme position indicated with dashed lines. The focus F of the shockwaves can be shifted with infinite variation between these two extreme positions, dependent on the position of the sleeve 44 along the acoustical axis A of the shockwave source 33, which corresponds to the center axis M. The adjustment mechanism may be provided with a position sensor (not shown), for example an inductive element, which supplies a signal via a line 93 corresponding to the position of the sleeve 44, and thus to the position which has been set for the focus F.

Because, when the sleeve 44 is adjusted, the volumes between the pressure pulse 34 and the entry wall 40 and between the entry wall 40 and the solid lens 38 will change, connecting sleeves 49 and 50 are respectively provided for those volumes, placing those volumes respectively in fluid communication with compensation vessels 51 and 52. The compensation vessel 51 contains acoustic propagation medium, such as water, and the compensation vessel 52 contains lens liquid. Volume compensation can thus ensue as needed both for the water 36 and the lens liquid 41.

A pressure sensor 53 is attached to that side of the solid lens 38 facing away from the pressure pulse source 34. The pressure sensor 53 may, for example, be a sensor formed by piezoelectrically-activated polymer foil, of the type sold by Pennwalt of Great Britain under the name "Kynar ®-Piezo-Film SDT 1-028 k." The pressure sensor 53 is electrically connected to an evaluation circuit 55 (shown in FIG. 1) via a line 54. The pressure pulse source 34 is electrically connected via a cable 56 to a high-voltage pulse generator 57 (shown in FIG. 1). When the pressure pulse source 34 is charged with a high voltage source from the generator 57 so as to cause the output of a shockwave, the pressure sensor 53 will supply two successive, pulse-like signals. The first of these signals arises as the pressure pulse emanating from the pressure pulse source 34 passes through the pressure sensor 53 on its way to the focus. The second of these signals arises due to portions of the shockwave which are reflected at the bone 12 to be treated pass through the pressure sensor 53.

As shown in FIG. 1, the apparatus includes a control unit 60 which coordinates the interaction of the individual apparatus components for implementing a treatment. The treatment of, for example, a femur fracture which is healing poorly because of inadequate callus formation, takes place in the following way.

The patient is first positioned so that the leg containing the fracture to be treated can be introduced into the coupling element 10. With the patient's leg introduced into the coupling element 10, the patient is then aligned so that the fracture is situated approximately in the middle of the coupling element in the axial direction. As described in conjunction with FIG. 3, the coupling element 10 is then applied to the leg by filling its interior with water and by charging the water with pressure.

A keyboard 61, connected to the control unit 60, is then actuated so as to activate the x-ray diagnostics system formed by the x-ray radiator 4 and the x-ray image intensifier 3 via the control unit 60. The control unit 60 activates the x-ray image intensifier 3 and the video camera (not shown) integrated therein via a control line 62, and also activates the high-voltage generator 28, and thus the x-ray radiator 4, via a control line 63. The video camera supplies a video signal in a known manner which corresponds to the transillumination image of the thigh 11. The video signal is supplied via a signal line 64 to an analog-to-digital converter 65. The digital output data of the analog-to-digital converter 65 corresponding to the video signal are entered in a memory 66, which is a write/read memory, having a capacity sufficient for storing two x-ray images. While data corresponding to the current x-ray image are entered into the memory 66, data corresponding to the preceding x-ray image are read out from the memory 66, and are supplied to a digital-to-analog converter 67 which generates a video signal which is supplied to a video monitor 68. This procedure is controlled by an electronic calculating unit 81 which, via clock lines 69 and 70, supplies clock signals to the analog-to-digital converter 65 and to the digital-to-analog converter 67. The calculating unit 81 also addresses the memory 66 via an address bus 71 and a control line 72 as necessary, and switches between write and read modes as necessary for writing and reading the data. A continuous display of the region of the thigh 11 situated in the beam path of the x-ray diagnostics system is thus generated.

Upon further actuation of the keyboard 61, the bracket 6 is displaced in either direction along the guide rod 8 so that, as shown in FIG. 1, the fracture comes to be located in the center of the x-ray image displayed on the video monitor 68. For this purpose, the control unit 60 appropriately actuates the drive unit 48 via a control line 73, causing suitable operation of the motor M2 connected to the drive unit 48 via a line 74. A position sensor 75 (not shown in detail, but which may be a digital rotational angle sensor) is connected to the motor M2 and supplies a signal on a signal line 76 to the control unit 60 which corresponds to the position of the bracket 6 on the guide rod 8.

If not already in the position shown in FIG. 1, the carrier 1 is rotated to that position so that the central ray Z of the x-ray beam proceeds approximately vertically. Such rotation is accomplished by appropriate actuation of the keyboard 61. A sensor 79 which may, for example, optically sense markings applied to the circumference of the carrier 1, supplies a signal to the control unit 60 via a signal line 78 which indicates the position of the carrier 1. The motor M1, which is connected to the drive unit 48 via a line 77, is actuated via the control unit 60 and via the drive unit 48 until the sensor 79 indicates that the desired position has been reached. When this occurs, the control unit 60 enables the electronic calculating means 81 via a control line 80 to cause the x-ray image which is generated in this position to be stored in the memory 66. When this has occurred, the control unit 60 operates the motor M1 via the drive unit 48, while monitoring the signal supplied by the sensor 79, until the carrier 1 has been rotated by a defined angle of, for example, 90°, and the central ray Z proceeds horizontally. When this has occurred, the control unit 60 enables the electronic calculating unit 81 to additionally cause the x-ray image obtained in this second position of the carrier 1 to be stored in the memory 66.

The data corresponding to the x-ray images produced in this manner are read from the memory 66 in succession, and are supplied to the digital-to-analog converter 67, as well as to a further digital-to-analog converter 82 which is connected to the electronic calculating unit 81 via a clock line 94. The electronic calculating unit 81 drives the digital-to-analog converters 67 and 82 so that the x-ray image corresponding to the vertically proceeding central ray Z is permanently displayed on the video monitor 68, and the x-ray image corresponding to the horizontally proceeding central ray Z is permanently displayed on another video monitor 83. A mark generator 84 is connected between the digital-to-analog converters 67 and the video monitor 68, and a mark generator 85 is connected between the digital-to-analog converters 82 and the video monitor 83. The mark generators each serve the purpose of mixing a line L into the respective video signals supplied by the digital-to-analog converters 67 and 82. The line L corresponds to the image of a plane which intersects the center axis of the carrier 1 at a right angle in the x-ray images displayed on the video monitors 68 and 83. The intersection of the plane with the center axis of the carrier 1, thus the position of the lines L in the x-ray image, is dependent on the position of a track ball (mouse) 86 which is connected to the electronic calculating unit 81. The electronic calculating unit 81 supplies output signals corresponding to the position of the track ball 86 to the mark generators 84 and 85 via a line 87.

With the track ball 86, the line L mixed into the x-ray images is then displaced so that, for example, it intersects the fracture break in the x-ray image displayed on the video monitor 68 at a point which is to be treated with shockwaves. For clarity, in the representative images shown on the video monitor 68 and 83 in FIG. 1, the fracture break is shown with that part facing toward the x-ray radiator 4 entered with a solid line and that part facing toward the x-ray image intensifier 3 entered dotted line. This point on the monitor 68 is now tapped with a light pen 88 connected to the electronic calculating unit 81. The corresponding point in the x-ray image displayed on the video monitor 83 is also tapped with the light pen 88, it being up to the attending physician to recognize which of the intersections of the mixed-in line L with the path of the fracture break corresponds to the previously tapped point. The electronic calculating unit 81 is supplied with data corresponding to the illustrated x-ray images via a data bus 89. Upon receiving the information via the light pen 88, the calculating unit 81 calculates the spatial position of the point identified in the two x-ray images by the light pen 88 according to a known algorithm, which is based on the fact that the x-ray images are produced by a central projection with intersecting central rays.

The calculating unit 81 forwards the result of its calculation to the control unit 60 via a data line 90. The control unit 60 actuates the motors M1 and M2 to bring the treatment head 2 into a position such that the acoustic axis A of the shockwave generator 5 proceeds through the point identified with the light pen 88, with this point lying directly opposite the treatment head 2. When signals from the position sensors 75 and 79 indicate that this position has been achieved, the control unit 60 activates the high-voltage pulse generator 57 via a control line 91 causing the high-voltage generator 57 to drive the shockwave source 33 to generate an output sequence of reduced-intensity shockwaves. The evaluation circuit 55 calculates the time which elapses between the pulse-like output signals of the pressure sensor 53, which occur following each reduced-intensity shockwave, as described above in connection with FIG. 2. Data corresponding to this elapsed time is supplied to the control unit 60 via a data line 92. From the supplied data, the control unit 60 calculates the distance of the pressure sensor 53 from the boundary layer between the femur 12 and the surrounding tissue, and actuates the adjustment mechanism 46 (FIG. 2) via the drive unit 48 and the line 47 so that the positive lens 35 has a focal length such that the focus F of the shockwaves lies in the boundary surface between the femur 12 and the surrounding tissue. The control unit 60 receives signals via the line 93 corresponding to the focal length which has been set in this manner.

After correctly setting the focal length of the positive lens 35, the control unit 60 actuates the high-voltage pulse generator 57 so that it drives the shockwave source 33 to generate shockwaves, having an intensity adapted to the particular treatment purpose. The intensity can be selected by actuation of the keyboard 61. After charging the point to be treated, in the manner described above, with a plurality of shockwaves (the number being pre-selectable with the keyboard 61), the next point to be treated is marked with the track ball 86, and identified with the light pen 88, in the manner described above, and the above procedure is repeated. The entire procedure is repeated until the fracture has been charged with shockwaves over its entire circumference, or in all desired points. The thigh can then be prepared and immobilized in a suitable way, for example with a plaster cast.

In a second mode selectable with the keyboard 61, the treatment procedure is undertaken with the path of the fracture break being traced with the light pen 88 in the x-ray images displayed on the video monitors 68 and 83. According to a known algorithm, the electronic calculating unit 81 then calculates the spatial path and the spatial position of the fracture break point-by-point, the density of the points being dependent on the number of lines in the video images supplied by the x-ray image intensifier. The calculating unit 81 forwards the corresponding data to the control unit 60, which controls adjustment of the position of the therapy head 2 so that the acoustic axis A of the shockwave source 33 successively proceeds to the individual points of the fracture break. For each individual point, the focal length of the positive lens 35 is first set in the necessary manner as described above using reduced-intensity shockwaves, followed by the generation of the selected number of shockwaves having an intensity selected for treatment purposes.

In both described modes, the setting of the focal length of the positive lens 35 can be done on the basis of the spatial position of the points of the fracture break calculated with the electronic calculating unit 81. The signals supplied by the pressure sensor 53 then serve only the purpose of monitoring and correcting the focal length which has been set. The pressure sensor 53 may possibly be eliminated, however, this is not desirable because at least a monitoring of the adjusted focal length of the positive lens 35 is desirable for patient safety.

Figure 4:
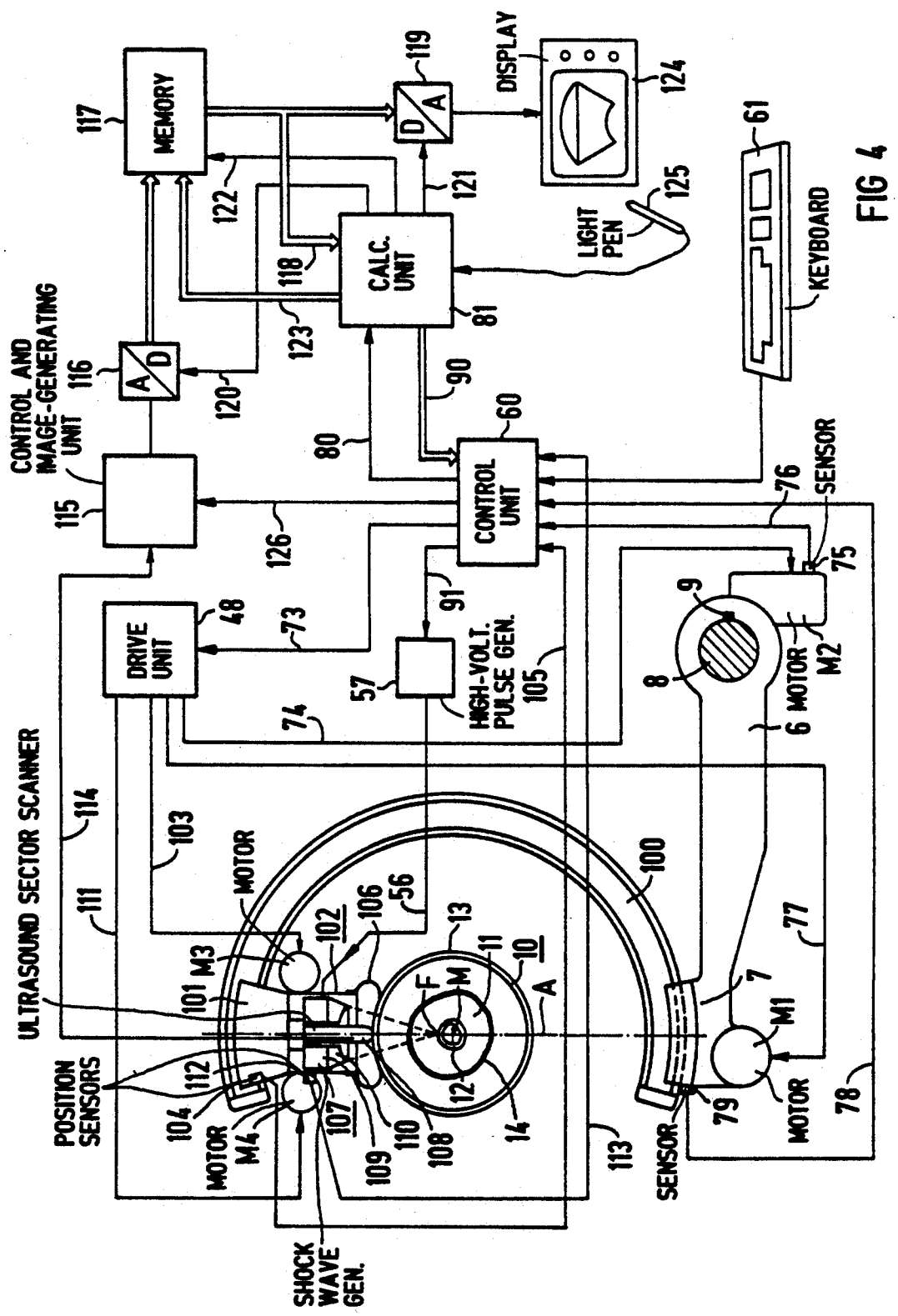
FIG. 4 is an end elevational view of a further embodiment of an apparatus for treating bone pathologies with acoustic waves constructed in accordance with the principles of the present invention, with associated electronic components being schematically indicated in a block diagram.

The embodiment of the apparatus shown in FIG. 4 has a number of components in common with the above-described exemplary embodiment, which are shown in FIG. 4 with the same reference symbols.

The apparatus in the embodiment of FIG. 4 includes a bracket 6 adjustable along a guide rod 8 with a motor M2, and a circularly curved carrier 100 received in the guide 7 of the bracket 6, which is adjustable along its circumferential direction by the motor M1. In contrast to the carrier 1, in the embodiment of FIG. 1, the carrier 100 does not extend over a full 360°, but instead extends only slightly more than 180°. The carrier 100 has a double T-shaped cross section. A therapy head, generally referenced 102, is provided with a guide 101 for attachment to the inner circumference of the carrier 100. The therapy head 102 is adjustable through 180° along the inside circumference of the carrier 100 by means of a motor M3 which interacts via gearing with teeth (not shown) attached to the inner circumference of the carrier 100. The guide 101 surrounds the inner flange of the carrier 100.

Because the carrier 100 is adjustable through 180° along its outer circumference in the guide 7 by means of the motor M1, it is possible to rotate the therapy head 102 through a total of 360° around the center axis M by a combined actuation of the motors M1 and M3. The motors M1, M2 and M3 are in electronic communication with the drive unit 48 via respective lines 77, 74 and 103. The drive unit 48 is connected to the control unit 60 via a control line 73, as in the embodiment of FIG. 1. In addition to the position sensors 75 and 79, a further position sensor 104 is provided in the embodiment of FIG. 4, which senses markings (not shown) provided at the inside circumference of the carrier 100, and serves the purpose of identifying the position of the therapy head 102 relative to the carrier 100. The position sensors 75, 79 and 104 are connected to the control unit 60 via respective signal lines 76, 78 and 105. The coupling element 10, fashioned according to FIG. 3, is again provided for accepting the body part 11 containing the bone 12 to be treated. The coupling element 10 is held so that its center axis M coincides with that of the carrier 100.

The therapy head 102 is constructed according to the teachings of U.S. Pat. No. 4,947,830, and includes a housing closed by a coupling pillow 106 pressing against the coupling element 10. The housing, for example, contains water as the acoustic propagation medium. A shockwave source generally referenced 107 and an ultrasound sector scanner 108 arranged in a central opening of the shockwave source 107 are situated in the interior of the housing. The shockwave source 107 includes a pressure pulse source 109 and an acoustic positive lens 110 disposed in front of the pressure pulse source 109. The positive lens 110 is a solid lens having a fixed focal length. The pressure pulse source 109 is electrically connected to the high-voltage pulse generator 57 via the line 56. When the pressure pulse source 109 is charged with high-voltage pulses by the high-voltage pulse generator 57, focused shockwaves are generated as an output, which converge in the focus F. In order to be able to shift the focus F along the acoustic axis A of the shockwave source 107, which intersects the center axis M of the carrier 100, a motor M4 is provided which displaces the shockwave source 107, i.e., the pressure pulse source 109 and the positive lens 110 in the housing of the therapy head 102 are displaced together along the acoustic axis A. The motor M4 is connected to the drive unit 48 via a line 111 and acts on the shockwave source 107 via a suitable gearing (not shown). For monitoring the position of the shockwave source 107, and thus the position of the focus F, a position sensor 112 is provided which is connected to the control unit 60 via a signal line 113. The position sensor 112 may, for example, be an inductively operating sensor.

The ultrasound sector scanner 108 generates ultrasound images of planes of the body part 11 to be treated which contain the acoustic axis A of the shockwave source 107, and thus also contain the focus F of the shockwaves and the center axis M of the carrier 100. Via a signal and control line 114, the ultrasound sector scanner 108 is in communication with a control and image-generating unit 115, of known construction and operation, which supplies an output in the form of a video signal corresponding to the ultrasound image of the scanned slice. This video signal proceeds to an analog-to-digital converter 116. The digital data corresponding to the video signal are supplied to an image memory 117, having a storage capacity sufficient for storing a plurality of ultrasound images, for example seventy-two ultrasound images. The output of the memory 117 which is a write/read memory, is in communication with a data bus 118 which leads to the electronic calculating unit 81 and to a digital-to-analog converter 119. The calculating unit 81 supplies clock signals to the analog-to-digital converter 116 and to the digital-to-analog converter 119 via respective clock lines 120 and 121. Via a control line 112, the calculating unit 81 also supplies signals for switching the memory 117 from a write mode to a read mode and vice versa. In order to be able to write and read data in the required manner, the calculating unit 81 is in communication with the memory 117 via an address bus 123. The video signal present at the output of the digital-to-analog converter 119 is supplied to a video monitor 124. A light pen 125, which is connected to the calculating unit 81, serves the purpose of marking specific regions in the image displayed on the video monitor 124. The electronic calculating unit 81 and the control unit 60 are in communication with each other via a data line 90 and a control line 80.

For treating, for example, a poorly healed fracture of the femur 12, the following procedure is used. After the coupling element 10 has been applied to the thigh 11, the motors M1 and M4 are actuated in response to suitable actuation of the keyboard 61, connected to the control unit 60, so that the therapy head 102 assumes the basic position shown in FIG. 4 with respect to the carrier 100, and the carrier 100 assumes the basic position shown in FIG. 4 with respect to the bracket 6. Additionally, the ultrasound sector scanner 108 is activated via the line 120 leading to the control and imaging unit 115 so as to continuously produce ultrasound images of the slice.

The video signals corresponding to the successively generated ultrasound images are digitized by the analog-to-digital converter 116 and are supplied to the memory 117, from which they are respectively immediately read out again and supplied to the digital-to-analog converter 119. Images corresponding to the video signals supplied by the digital-to-analog converter 119 then appear on the video monitor 124. While observing these images, the attending physician operates the keyboard 61 to cause the bracket 6 to be moved in the appropriate direction along the guide rail 8 so that the fracture comes to be located within the slice shown in the ultrasound images. When this occurs, data corresponding to the most recently generated image are continuously read out from the memory 117 in response to an appropriate actuation of the keyboard 61, so that the most recently produced ultrasound image is continuously displayed on the video monitor 124. The region of the fracture shown in the ultrasound image is now tapped with the light pen 125. In a known manner, the calculating unit 81 calculates the position to which the bracket 6 must be moved, proceeding from its existing position, so that the acoustic axis A of the shockwave source 107 proceeds through the region of the fracture marked with the light pen 125. The calculating unit 81 forwards corresponding data to the control unit 60 which causes the bracket 6 to be displaced to the calculated position in response to an appropriate actuation of the keyboard 61.

When this has been accomplished, another ultrasound image is generated and displayed on the video monitor 124. The data corresponding to the ultrasound image are now evaluated by the calculating unit 81 in a known manner so that the calculating unit 81 identifies that position along the acoustic axis A at which an intensity discontinuity occurs, corresponding to the boundary layer between the femur 12 and the surrounding tissue. The calculating unit 81 forwards the corresponding data to the control unit 60 which, in response thereto, actuates the motor M4 via the drive unit 48 while monitoring the signals supplied by the position sensor 112 so that the focus F of the shockwave source 107 is moved along the acoustic axis A into that position at which the discontinuity occurs, and thus at which the boundary surface between the femur 12 and the surrounding tissue lies. Although not shown in the drawings, a mark such as a graticule can be mixed in a simple manner into the respective ultrasound image, the mark indicating the current position of the focus F, so that it is possible to monitor the automatically-set position of the focus F. When the focus F is appropriately positioned, the control unit 60 activates the high-voltage pulse generator 57 via the control line 91 to cause the shockwave source 102 to generate a pre-selected plurality of shockwaves. The number and intensity of the shockwaves can be selected with the keyboard 61.

After application of the pre-selected plurality of shockwaves, the control unit 60, in response to actuation of the keyboard 61, displaces the treatment head 102 by a defined angle of, for example, 5° along the carrier 100 in the clockwise direction, whereupon the above procedure is repeated, for the region of the fracture visible in the ultrasound image, and after displacing the bracket 6 along the guide rod 8, if necessary. After the therapy head 102 has been displaced through 180° along the carrier 100, the carrier 100 is displaced in the guide 7 in 5° steps until the therapy head 102 has been conducted around the thigh 11 through a full 360°. The coupling element 10 is then separated from the thigh 11, and the "new fracture" which has arisen as a consequence of the (at least) partial disintegration of the bone due to the action of the shockwaves is re-set if necessary, and the thigh 11 is immobilized in a suitable way, for example with a plaster cast.

In a second mode selectable with the keyboard 61, the therapy head is first conducted around the thigh 11 in 5° steps. An ultrasound image is generated for each of the seventy-two positions. These ultrasound images are stored in the memory 117. Thereafter, the generated ultrasound images are successively displayed on the video monitor 124 by suitable actuation of the keyboard 61, and the region of the fracture shown in each ultrasound image is tapped with the light pen 125. Using the data acquired in this manner, the calculating unit 81 calculates the spatial path and the spatial position of the fracture point-by-point in a known manner. The plurality of points is limited to the points identified in the ultrasound images. Additional points, however, can be calculated on the basis of suitable interpolation methods, for example linear interpolation.

The calculating unit 81 forwards the corresponding data to the control unit 60, which controls adjustment of the therapy head 102 so that the acoustic axis A of the shockwave source 107 proceeds successively through the individual points of the fracture. With reference to the intensity discontinuity corresponding to the boundary surface between the bone and surrounding tissue in an ultrasound image as described above, the shockwave source 107 is first displaced in the direction of the acoustic axis A for each calculated point such that the focus F of the shockwaves lies in the aforementioned boundary surface. Subsequently, the plurality of shockwaves which has been selected is applied with an intensity which has also been selected. The ultrasound images which serve the purpose of setting the position of the focus F along the acoustic axis A can be either those ultrasound images which were produced in conjunction with the identification of the spatial path and the spatial position of the fracture, or ultrasound images which are additionally produced immediately before the application of the shockwaves. If additional points of the fracture were calculated by interpolation, such additional ultrasound images would have to be produced in any event.

In both operating modes, insofar as no interpolation was done in the second operating mode, the adjustment of the position of the focus along the acoustic axis A can ensue only on the basis of the spatial position of the points of the fracture which were calculated by the calculating unit 81. Data obtained on the basis of the intensity discontinuity then serve only for monitoring and correcting the position of the focus which has been set. Again, it is possible to forego the identification of the position of the focus with respect to the intensity discontinuity, however, this is not desirable because monitoring and possible correction are then also foregone, which decreases the patient safety.

The above-described exemplary embodiments have been set forth in the context of using an electromagnetic shockwave source as the source for acoustic waves. Other shockwave sources, for example a piezoelectric shockwave source, can be employed instead. Moreover, the acoustic waves which charge the bones to be treated need not necessarily be shockwaves. Other waves, sometimes referred to as rare faction pulses (which are waves having a negative, or less than atmospheric, pressure) or continuous sound may be used. In the exemplary embodiment of FIGS. 1 and 2, the x-ray radiator 4 and the shockwave generator 5 are rigidly joined to each other. It is also possible, however, to attach the shockwave generator 5 to the carrier 1 with a suitable carriage so that it can be adjusted along the circumference of the carrier 1, at least to an extent so that it can be completely moved out of the beam path of the x-ray beam emanating from the x-ray radiator 4. In this case, overview exposures of the body part to be treated can be produced with an x-ray film cassette, or with an x-ray image intensifier 3 having a sufficient diameter. Additional possibilities for optimally adapting the therapy method to a particular case are also available under certain circumstances due to the described adjustability of the shockwave generator 5.

Although further modifications and changes may be suggested by those skilled in the art, it is the intention of the inventor to embody within the patent warranted hereon all changes and modifications as reasonably and properly come within the scope of his contribution to the art.

I claim as my invention:

1. An apparatus for treating bone pathologies in situ with acoustic energy comprising:
   a source of focused acoustic waves;
   means for displacing the focus of said acoustic waves;
   means for locating the boundary surface between a bone to be treated with said acoustic waves and surrounding tissue and for generating signals corresponding to the position of said boundary surface; and
   control means, supplied with said signals, for actuating and controlling said means for displacing the focus for maintaining said focus substantially in said boundary surface independently of the position of said source while treating said bone with said acoustic waves.

2. An apparatus as claimed in claim 1 wherein said source of acoustic waves has an acoustic axis and wherein said focus lies on said acoustic axis, wherein said means for locating includes means for identifying the intersection of said acoustic axis and said boundary surface, and wherein said means for displacing is a means for displacing the focus of said acoustic waves along said acoustic axis to cause said focus and said intersection to substantially coincide.

3. An apparatus as claimed in claim 1 further comprising:
   means for adjusting the position of said source of focused acoustic waves operated by said control means;
   wherein said means for locating includes means for identifying the path of a zone of said bone to be treated and for generating signals, supplied to said control means, corresponding to said path of said zone; and
   wherein said control means includes means for operating said means for adjusting said source so that said source is adjusted in at least one degree of freedom with said focus always located in said zone to be treated independently of the position of said source with respect to other degrees of freedom.

4. An apparatus as claimed in claim 3 wherein said means for operating said means for positioning said source operates said means for positioning so that said focus is always located in a region of said zone to be treated which is closest to said source.

5. An apparatus as claimed in claim 3 wherein said means for operating said means for positioning said source operates said means for positioning to move said focus along said path of said zone to be treated.

6. An apparatus as claimed in claim 1 further comprising:
said means for locating including a pressure sensor disposed in the propagation path of said acoustic waves;
means for pulse-like actuating said source for causing said source to generate at least one pulse-like acoustic wave, said pulse-like acoustic wave causing said pressure sensor to generate a first pulse-like output signal as said pulse-like acoustic wave propagates toward said bone to be treated and causing said pressure sensor to generate a second pulse-like output signal upon reflection of said pulse-like acoustic wave; and
means for measuring the time between said first and second pulse-like output signals of said pressure sensor.

7. An apparatus as claimed in claim 6 wherein said means for actuating said source to generate at least one pulse-like acoustic wave is a means for actuating said source to generate at least one pulse-like acoustic wave having an intensity which is reduced in comparison to acoustic waves generated for treatment of said bone.

8. An apparatus as claimed in claim 1 wherein said means for locating comprises:
means for generating a plurality of ultrasound image slices each containing said focus;
means for identifying an intensity discontinuity in each of said slices corresponding to said boundary layer; and
means for comparing the location of said intensity discontinuity to the location of said focus in each ultrasound slice.

9. An apparatus as claimed in claim 1 further comprising:
means for adjusting the position of said source of focused acoustic waves, operated by said control means;
wherein said means for locating includes ultrasound means for generating an ultrasound slice having a defined position relative to said source;
means for marking a region of said bone to be treated contained in the said ultrasound slice, and means for generating signals corresponding to said marked region; and
electronic calculating means, to which said signals corresponding to said marked region are supplied, for calculating a set of control signals and supplying said control signals to said control means for operating said means for positioning said source such that said focus lies in the marked region.

10. An apparatus as claimed in claim 9 wherein said ultrasound means includes an ultrasound applicator, and wherein said ultrasound means generates a plurality of said slices at respectively different positions of said ultrasound applicator relative to said bone to be treated, said apparatus further comprising an image memory in which said plurality of ultrasound images are stored, and wherein said electronic calculating means includes means for calculating the spatial path and spatial position of at least one of a zone of said bone to be treated or said boundary surface within said zone to be treated with respect to said marked region, and wherein said spatial path and said spatial position comprise said control signals for operating said means for adjusting the position of said source.

11. An apparatus as claimed in claim 9 wherein said ultrasound means includes an ultrasound applicator, and wherein said source of focused acoustic waves has a central bore in which said ultrasound applicator is received.

12. An apparatus as claimed in claim 1 wherein said means for locating includes means for generating an x-ray beam in which said bone to be treated is disposed, and a radiation receiver disposed to receive said x-ray beam attenuated by said bone to be treated and for generating an x-ray image from the received radiation, and means for moving said means for generating an x-ray beam and said radiation receiver in coordination to produce a plurality of said x-ray images from different angles.

13. An apparatus as claimed in claim 12 further comprising:
an image memory for storing two of said x-ray images obtained at respectively different angles;
means for marking a path of a zone of said bone to be treated in said x-ray images and for generating signals corresponding to the marked path; and
electronic calculating means, supplied with said signals corresponding to said marked path, for calculating the spatial path and spatial position of at least one of said zone or said boundary surface within said zone, and for generating signals supplied to said control means for actuating and controlling said means for displacing the focus.

14. An apparatus as claimed in claim 1 further comprising means for adjusting the position of said source of focused acoustic waves along a circular path surrounding said bone to be treated while treating said bone with said acoustic waves.

15. An apparatus as claimed in claim 14 further comprising means for adjusting the position of said source along an axis which intersects a plane containing said circular path at a right angle while treating said bone with said acoustic waves.

16. An apparatus as claimed in claim 1 wherein said source of focused acoustic waves has an acoustic axis, and wherein said means for displacing the focus is a means for displacing said source along said acoustic axis.

17. An apparatus as claimed in claim 1 wherein said means for displacing the focus comprises:
an acoustic lens having a variable focal length contained in said source of focused acoustic waves; and
means for adjusting said focal length of said acoustic lens.

18. An apparatus as claimed in claim 1 wherein said means for locating the boundary surface between said bone to be treated with acoustic waves and surrounding tissue is a means for ultrasonically locating said boundary surface.

19. An apparatus as claimed in claim 1 wherein said means for locating the boundary surface between said bone to be treated with said acoustic waves and surrounding tissue is a means for radiologically locating said boundary surface.

20. An apparatus as claimed in claim 1 further comprising:
means for immobilizing said bone to be treated with acoustic waves.

21. An apparatus as claimed in claim 1 further comprising:
means for immobilizing said bone to be treated, said means for immobilizing having an outer surface;
means for adjusting the position of said source of focused acoustic shockwaves along a circular path surrounding said means for immobilizing; and
means for coupling said acoustic waves from said source of focused acoustic waves into said means for immobilizing, said means for coupling being in contact with said outer surface of said means for immobilizing and sliding over said outer surface as said source is adjusted along said circular path.

22. An apparatus as claimed in claim 1 wherein said source of focused acoustic waves is a source of focused shockwaves.

23. A method for treating bone pathologies in situ with acoustic waves comprising the steps of:
generating focused acoustic waves;
locating the boundary surface between a bone to be treated with said acoustic waves and surrounding tissue and generating signals corresponding to the position of said boundary surface; and
displacing said focus, based on said signals, to maintain said focus substantially in said boundary surface independently of the position of said source while treating said bone with said acoustic waves.

24. A method as claimed in claim 23 wherein the step of generating focused acoustic waves is further defined by generating focused acoustic waves propagating along an acoustic axis, wherein the step of locating said boundary surface is further defined by identifying the intersection of said acoustic axis and said boundary surface, and wherein the step of displacing said focus is further defined by displacing said focus along said acoustic axis to cause said focus and said intersection to substantially coincide.

25. A method as claimed in claim 23 wherein the step of generating focused acoustic waves is further defined by generating focused acoustic waves emanating from a source, wherein the step of locating said boundary surface is further defined by identifying the path of a zone of said bone to be treated and generating signals corresponding to said path of said zone, and wherein the step of displacing said focus is further defined by adjusting the position of said source and thereby displacing said focus so that said source is adjusted in at least one degree of freedom with said focus always located in said zone to be treated independently of the position of said source with respect to other degrees of freedom.

26. A method as claimed in claim 25 wherein the step of displacing said focus is further defined by adjusting the position of said source so that said focus is always located in a region of said zone to be treated which is closest to said source.

27. A method as claimed in claim 25 wherein the step of displacing said focus is further defined by adjusting the position of said source to move said focus along said path of said zone to be treated.

28. A method as claimed in claim 23 comprising the additional steps of:
generating at least one of said acoustic waves as a pulse-like acoustic wave;
identifying a first point in time at which said pulse-like acoustic waves passes a selected location as said pulse-like acoustic wave propagates toward said bone to be treated;
identifying a second point in time at which said pulse-like acoustic wave again passes said selected location after being reflected; and
measuring the duration between said first and second points in time.

29. A method as claimed in claim 28 wherein the steps of identifying said first and second points in time are further defined by identifying said first and second points in time using a pressure sensor disposed in the propagation path of said pulse-like acoustic wave.

30. A method as claimed in claim 28 wherein the step of generating said at least one pulse-like acoustic wave is further defined by generating at least one pulse-like acoustic wave having an intensity which is reduced in comparison to acoustic wave generated for treatment of said bone.

31. A method as claimed in claim 23 wherein the step of locating said boundary surface is further defined by ultrasonically locating said boundary surface.

32. A method as claimed in claim 31 comprising the additional steps of:
generating a plurality of ultrasound image slices each containing said focus;
identifying an intensity discontinuity in each of said slices corresponding to said boundary layer; and
comparing the location of said intensity discontinuity to the location of said focus in each ultrasound slice for locating said boundary surface.

33. A method as claimed in claim 31 wherein the step of generating focused acoustic waves is further defined by generating focused acoustic waves emanating from a source, and comprising the additional steps of:
generating an ultrasound slice having a defined position relative to said source;
marking a region of said bone to be treated contained in said ultrasound slice and generating signals corresponding to said marked region; and
adjusting the position of said source, based on said signals corresponding to said marked region, to position said source so that said focus lies in said marked region.

34. A method as claimed in claim 31 wherein the step of ultrasonically locating said boundary surface is further defined by ultrasonically locating said boundary surface using an ultrasound field generated by an ultrasound applicator, and comprising the additional steps of:
generating a plurality of said ultrasound slices at respectively different positions of said ultrasound applicator relative to said bone to be treated;
storing said plurality of ultrasound images;
calculating the spatial path and spatial position of at least one of a zone of said bone to be treated or said boundary surface within said bone to be treated with respect to said marked region; and
adjusting the position of said source based on said spatial path and said spatial position calculations.

35. A method as claimed in claim 23 wherein the step of locating said boundary surface is further defined by radiologically locating said boundary surface.

36. A method as claimed in claim 35 wherein the step of radiologically locating the boundary surface is further defined by generating a plurality of x-ray images of said bone to be treated from different angles.

37. A method as claimed in claim 36 comprising the additional steps of:
   storing two of said x-ray images obtained at respectively different angles;
   marking a path of a zone of said bone to be treated in said x-ray images and generating signals corresponding to the marked path; and
   calculating a spatial path and spatial position of at least one of said zone or said boundary surface within said zone, and displacing said focus based on said spatial path and spatial position calculations.

38. A method as claimed in claim 23 wherein the step of generating focused acoustic waves is further defined by generating focused acoustic waves emanating from a source, and comprising the additional step of:
   moving said source along a circular path surrounding said bone to be treated while treating said bone with said acoustic waves.

39. A method as claimed in claim 38 comprising the additional step of:
   moving said source along an axis which intersects the plane containing said circular path at a right angle while treating said bone with said acoustic waves.

40. A method as claimed in claim 23 wherein the step of generating focused acoustic waves is further defined by generating focused acoustic waves emanating from a source and propagating along an acoustic axis, and wherein the step of displacing said focus is further defined by displacing said source along said acoustic axis.

41. A method as claimed in claim 23 wherein the step of generating focused acoustic waves is further defined by generating focused acoustic waves using a variable focal length acoustic lens, and wherein the step of displacing said focus is further defined by displacing said focus by adjusting said focal length of said acoustic lens.

42. A method as claimed in claim 23 comprising the additional step of:
   immobilizing said bone to be treated.

43. An apparatus for treating bone pathologies in situ with acoustic energy comprising:
   a source of focused acoustic waves propagating along an acoustic axis, including an acoustic lens with an adjustable focal length;
   means for adjusting the position of said source along said acoustic axis;
   means for generating an x-ray beam in which a bone to be treated is disposed;
   means for detecting said x-ray beam, attenuated by said bone, and for generating an x-ray image of said bone;
   means for moving said means for generating an x-ray beam and said means for detecting said x-ray beam around said bone for generating two of said x-ray images from respective positions offset by a known angle;
   means for identifying the three-dimensional position and extent of a selected feature in said two x-ray images having a relationship to the boundary surface between said bone and surrounding tissue, and for generating signals corresponding thereto;
   means for moving said source around said bone in a plane while treating said bone with said acoustic waves;
   means for moving said source along an axis perpendicular to said plane; and
   means, supplied with said signals, for coordinating movement of said source around said bone and along said perpendicular axis and simultaneously controlling adjustment of at least one of said focal length of said acoustic lens or said position of said source along said acoustic axis for maintaining said focus in said boundary layer while treating said bone with acoustic waves.

44. An apparatus for treating bone pathologies in situ with acoustic energy comprising:
   a source of focused acoustic waves propagating along an acoustic axis;
   means for adjusting the position of said source along said acoustic axis;
   an ultrasound applicator for generating an ultrasound field in which a bone to be treated is disposed;
   means for processing signals from said ultrasound applicator to generate an ultrasound image of said bone;
   means for moving said ultrasound applicator to generate a plurality of said ultrasound images from different positions;
   means for identifying the three-dimensional position and extent of a selected feature in said plurality of ultrasound images having a relationship to the boundary surface between said bone and surrounding tissue, and for generating signals corresponding thereto;
   means for moving said source around said bone in a plane while treating said bone with said acoustic waves;
   means for moving said source along an axis perpendicular to said plane; and
   means, supplied with said signals, for coordinating movement of said source around said bone and along said perpendicular axis and simultaneously controlling adjustment of said position of said source along said acoustic axis for maintaining said focus in said boundary layer while treating said bone with acoustic waves.

* * * * *